US00PP07843P

United States Patent [19]

Zaiger et al.

[11] Patent Number: Plant 7,843

[45] Date of Patent: Mar. 31, 1992

[54] PLUM TREE "AUTUMN PRIDE"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 616,381

[22] Filed: Nov. 21, 1990

[51] Int. Cl.[5] ..... A01H 5/00

[52] U.S. Cl. ..... Plt./38

[58] Field of Search ..... Plt. 38

*Primary Examiner*—James R. Feyrer

[57] ABSTRACT

A new and distinct variety of plum tree which has the following combination of desirable features that are outstanding in a new variety.

1. Late maturity of fruit.
2. Heavy and regular production.
3. Very good flavor and eating quality.
4. Fruit with good storage and shipping quality.
5. Fruit that will hold firm on the tree for approximately 2 weeks after maturity.
6. Uniform coloring of the skin giving the fruit an attractive appearance.
7. Upright vigorous growth.
8. Fruit with attractive plum-purple to dark violet color.

1 Drawing Sheet

ORIGIN OF THE VARIETY

The herein described variety of plum tree was originated by us in the experimental orchard, located near Modesto, Calif. as a cross between Friar Plum (non-patented) and a selected seedling with the field identification number "59GA511". The pollen parent "59GA511" originated as a selected seedling from a cross between Mariposa Plum (non-patented) and Ebony Plum (U.S. Plant Pat. No. 2,049).

ASEXUAL REPRODUCTION OF THE VARIETY

The new variety of plum tree was asexually propagated by budding, as performed by us in the experimental orchard located near Modesto, Calif. and shows that all characteristic traits come true to the original tree and are transmitted through succeeding asexual propagations.

SUMMARY OF THE VARIETY

Our new and distinct variety of plum tree which is of large size, vigorous, upright in growth and a regular and productive bearer of large size, firm flesh, semi-freestone fruit with very good flavor and eating quality. The tree is further characterized by producing late maturing fruit, ripening 7-10 days after Roysum Plum (U.S. Plant Pat. No. 2,619) one of the latest commercial varieties.

BRIEF DESCRIPTION OF THE PHOTOGRAPHS

The accompanying photographic illustrations show typical specimens of the foliage and fruit of our new plum variety, with the upper and lower surface of the leaves being illustrated, an exterior and sectional view of the fruit being shown with a stone remaining in place. The photographs were taken shortly after the fruit was picked at maturity (firm ripe) and the colors are as nearly true as reasonably possible in a color photograph of this type.

DESCRIPTION OF THE VARIETY

The following is a detailed botanical description of our new and distinct variety of plum tree, its foliage, flowers and fruit with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearer.*—Regular.

Trunk:
- *Size.*—Medium.
- *Surface.*—Medium shaggy to shaggy.
- *Lenticels.*—Medium number. Size — large.
- *Color.*—Brown to coffee brown (5-F-7) to (5-F-8).

Branches:
- *Size.*—Medium stocky.
- *Surface.*—Smooth to medium shaggy.
- *Lenticels.*—Medium number. Large size.
- *Color.*—Brown to grayish brown.

Leaves:
- *Size.*—Medium. Average length — 3½" to 4". Average width — 1⅛" to 1⅜".
- *Form.*—Oblanceolate. Pointed.
- *Texture.*—Smooth.
- *Petiole.*—Average length — ¾". Medium thickness.
- *Margin.*—Serrulate.
- *Glands.*—Number varies 1 to 3. Average number 2.
- *Color.*—Upper surface — green to deep green (28-E-7) to (28-F-7). Lower surface — green to grayish green (28-D-6) to (28-E-6).

Flower buds:
- *Size.*—Small to medium.
- *Length.*—Medium.
- *Form.*—Plump.

Flowers:
- *Blooming period.*—Date of first bloom: Feb. 27, 1989. Date of last bloom: Mar. 9, 1989. Varies slightly with climatic conditions. Blooms approximately 2 days before Santa Rosa Plum.
- *Size.*—Medium.
- *Color.*—White.

Fruit:

*Maturity when described.*—Shipping ripe.
*Date of first picking.*—Sept. 27, 1989.
*Date of last picking.*—Oct. 2, 1989.
*Size.*—Large. Average diameter axially — $2\frac{1}{2}''$ to $2\frac{5}{8}''$. Average transversely in suture plane — $2\frac{3}{8}''$ to $2\frac{1}{2}''$.
*Form.*—Nearly Globose, only slightly flattened at apex and stem end.
*Suture.*—Shallow — extends from base to apex.
*Base.*—Nearly rounded, only slightly retuse.
*Apex.*—Nearly rounded, only slight depression.
*Cavity.*—Size — small. Rounded — slightly elongated in suture plane. Average depth — $\frac{1}{4}''$. Average breadth — $\frac{3}{8}''$.
*Stem.*—Short. Medium width.

Skin:
*Thickness.*—Medium.
*Texture.*—Medium.
*Tendency to crack.*—Very slight.
*Down.*—Wanting.
*Bloom.*—Moderate.
*Color.*—Plum purple to dark violet (15-F-5) to (15-F-8).

Flesh:
*Ripens.*—Evenly.
*Flavor.*—Very good, mild, sweet, good balance between sugar and acid.
*Texture.*—Firm, meaty.
*Aroma.*—Slight.
*Eating quality.*—Very good.
*Color.*—Pale yellow to light yellow — (4-A-3) to (4-A-5).

Stone:
*Type.*—Semi-freestone.

*Form.*—Ovid.
*Size.*—Medium. Average length — $1''$. Average width — $\frac{3}{4}''$. Average thickness — $\frac{1}{2}''$.
*Base.*—Straight.
*Apex.*—Acuminate.
*Sides.*—Nearly equal.
*Surface.*—Only slightly furrowed. Pitted near the edges, heavier near suture plane.
*Tendency to split.*—None.
*Color.*—Light brown to grayish brown (6-C-4) to (6-D-4).

Use:
*Market.*—Local and long distance. Dessert.

Keeping quality: Good.
Shipping quality: Good.

The plum tree, its flowers, foliage and fruit herein described may vary in slight detail due to climatic, soil and ecological conditions under which the variety may be grown; the present description being that of the variety grown under the conditions in the experimental orchard located near Modesto, Calif.

The following is claimed:

1. A new and distinct variety of plum tree, substantially as illustrated and described, characterized by its vigorous, upright growth and a regular and productive bearer of large, firm, semi-freestone fruit with very good flavor and eating quality; the tree is particularly characterized by bearing fruit which mature in the very late season, approximately 7 to 10 days after Roysum Plum (U.S. Plant Pat. No. 2,619) one of the latest maturing commercial varieties.

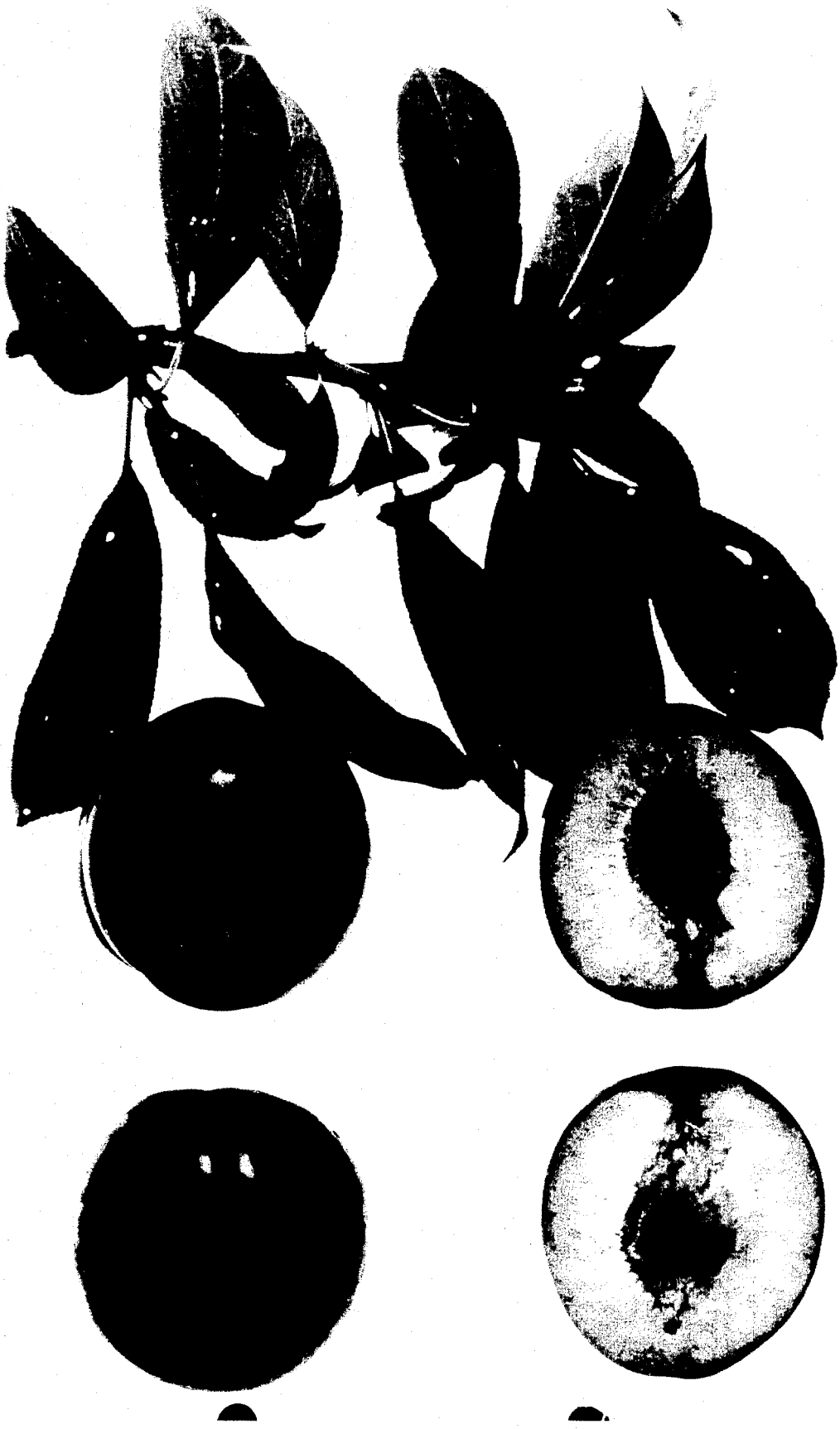

* * * * *